United States Patent [19]
Gallagher

[11] Patent Number: 5,448,072
[45] Date of Patent: Sep. 5, 1995

[54] INFRARED HOT BEARING AND HOT WHEEL DETECTOR

[75] Inventor: Cornelius A. Gallagher, Syosset, N.Y.

[73] Assignee: Servo Corporation of America, Hicksville, N.Y.

[21] Appl. No.: 111,159

[22] Filed: Aug. 24, 1993

[51] Int. Cl.$^6$ .............................................. B61K 9/06
[52] U.S. Cl. .................................. 250/349; 250/342; 246/169 A; 246/169 D
[58] Field of Search ............................. 250/342, 349; 246/169 A, 169 D

[56] References Cited

U.S. PATENT DOCUMENTS

| | | | |
|---|---|---|---|
| 3,206,596 | 9/1965 | Howell | 246/169 D |
| 3,253,140 | 5/1966 | Sibley et al. | 246/169 D |
| 5,331,311 | 7/1994 | Doctor | 246/169 A |

FOREIGN PATENT DOCUMENTS 41178 12/1981 European Pat. Off. ........ 246/169 A

*Primary Examiner*—Carolyn E. Fields
*Attorney, Agent, or Firm*—Kane, Dalsimer, Sullivan, Kurucz, Levy, Eisele and Richard

[57] ABSTRACT

A detector apparatus uses two scanners on the right of way for monitoring the wheels of a moving train. The scanners scan the wheels transversely to the tracks along a common axis and generate wheel temperature signals. The signals corresponding to the wheel bearing end caps or housing lids indicative of the wheel bearing temperatures are separated and analyzed so that the apparatus can detect and indicate both hot wheel and hot bearing conditions.

20 Claims, 3 Drawing Sheets

INFRARED HOT BEARING AND HOT WHEEL DETECTOR

BACKGROUND OF THE INVENTION

A. Field of Invention

This invention pertains to an apparatus for monitoring railroad trains, and more specifically to an infrared apparatus for detecting hot bearings and hot wheels of a train.

B. Description of the Prior Art

A major source of problems in the field of railroad transportation and especially freight railroad trains have been overheated bearings. An overheated bearing on a single car truck may cause the wheel journal to break, causing the car to overturn and the train to derail. Such derailments are extremely dangerous, and can cause immense economic expense. In order to prevent such derailments, infrared hot bearing detecting apparatuses are presently in service on railroads in virtually every major country in the world. The original system for these detectors was installed in the United States in 1956. Typically, such systems use an infrared scanner disposed on the railroad bed adjacent to the track and oriented at an angle upwardly so that it scans successively the bearing assemblies or housings and the bottom of the railroad car. The readings obtained from the car bottom are used as an indicia of the ambient temperature. Over the years various changes have been made in the design of railroad cars and the detectors must have the ability to scan and accurately measure the temperature of the bearings on a large number of car configurations. Existing detectors have problems accomplishing this task successfully. For example, the latest articulated freight cars do not present a uniform bottom to the scanner which can be used as an accurate ambient temperature reference, particularly when empty or partially loaded. Another problem with existing detectors has been that the bottom of empty hopper type freight cars may get heated up by the sun giving a false indication of the ambient temperature. In addition, radiation from the heated ballast in the summer raises the temperature of the car bottoms.

Another problem for railroads results from overheated wheels due to defective brake mechanisms or unreleased handbrakes. These mechanisms heat the wheels of a car to dangerous levels, causing the wheels to lose their tensile strength. Of course the dangerous temperature limit for a hot wheel is much higher than the dangerous temperature limit for a hot bearing and therefore a temperature for a wheel may be perfectly acceptable but may be too high for a bearing. Until now, this and other various physical constraints dictated the use of separate hot wheel and hot bearing detectors. In fact, many hot bearing detectors included means for occluding any hot wheel readings to insure that a normal wheel reading does not result in a false hot bearing reading. Of course a false hot bearing reading (or for that matter, a false hot wheel reading), while not as dangerous, is also very expensive if it results in the stopping of a train. False train stops in the application of prior art hot bearing detectors are the greatest detriment to the application of hot bearing detectors.

U.S. Pat. No. 2,818,508 to Johanson et al. discloses a hot bearing detector with a scanner oriented transversely to the train movement, and a wheel sensor which disables the scanner to insure that hot wheel readings are excluded.

U.S. Pat. No. 3,545,005 to Gallagher discloses a hot bearing detector with a mechanical shutter operated by a wheel.

U.S. Pat. No. 3,253,140 to Sibley et al. discloses a system with an angled detector for recording the temperature of a wheel hub, wheel web and wheel rim.

OBJECTIVES AND SUMMARY OF THE INVENTION

In view of the above-mentioned disadvantages of the prior art, it is an objective of the present invention to provide a single detector for detecting both hot wheels and hot bearings on a moving railroad car.

A further objective is to provide a detector with an accurate ambient temperature reference, which is unaffected by hot car bottoms or inadvertent sky readings.

Yet a further objective is to provide a detector for monitoring bearings of railroad cars having different types of bearing/truck configurations, including types not adequately scanned by existing detectors.

A further objective is to provide a detector with the ability of virtually eliminating false indications by scanning wheels and bearings sequentially and isolating the readings obtained thereof by signal gating means.

Other objectives and advantages of the invention shall become apparent from the following description. Briefly, a detector apparatus constructed in accordance with this invention consists of a scanner positioned and arranged to monitor the wheels and bearing structures of a railroad car in a direction normal to the wheel movement. The temperature of both the wheel rims and wheel bearings (as indicated by the bearing end cap or housing) are sequentially fed to an analyzing means which gates the signals respectively to a hot wheel and a hot bearing analyzing section.

Preferably, a second scanner is positioned across the track with the two scanners having a common optical axis. The second scanner presents a surface which is used by the first scanner to determine the ambient temperature reference against which the bearing and wheel signal is compared.

DETAILED DESCRIPTION OF THE INVENTION

Figure 1:
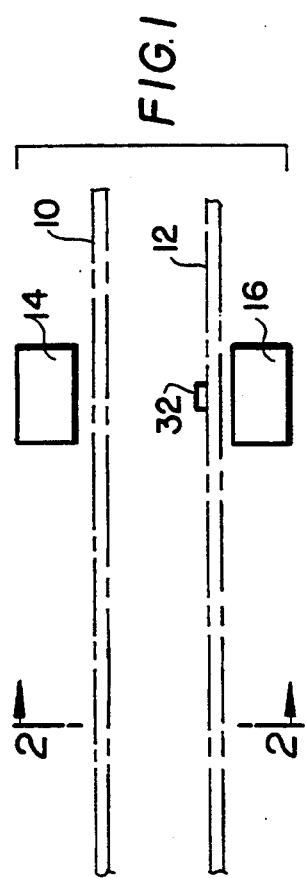
FIG. 1 shows a plan view of a railroad track with a detector apparatus constructed in accordance with this invention.
Figure 2:
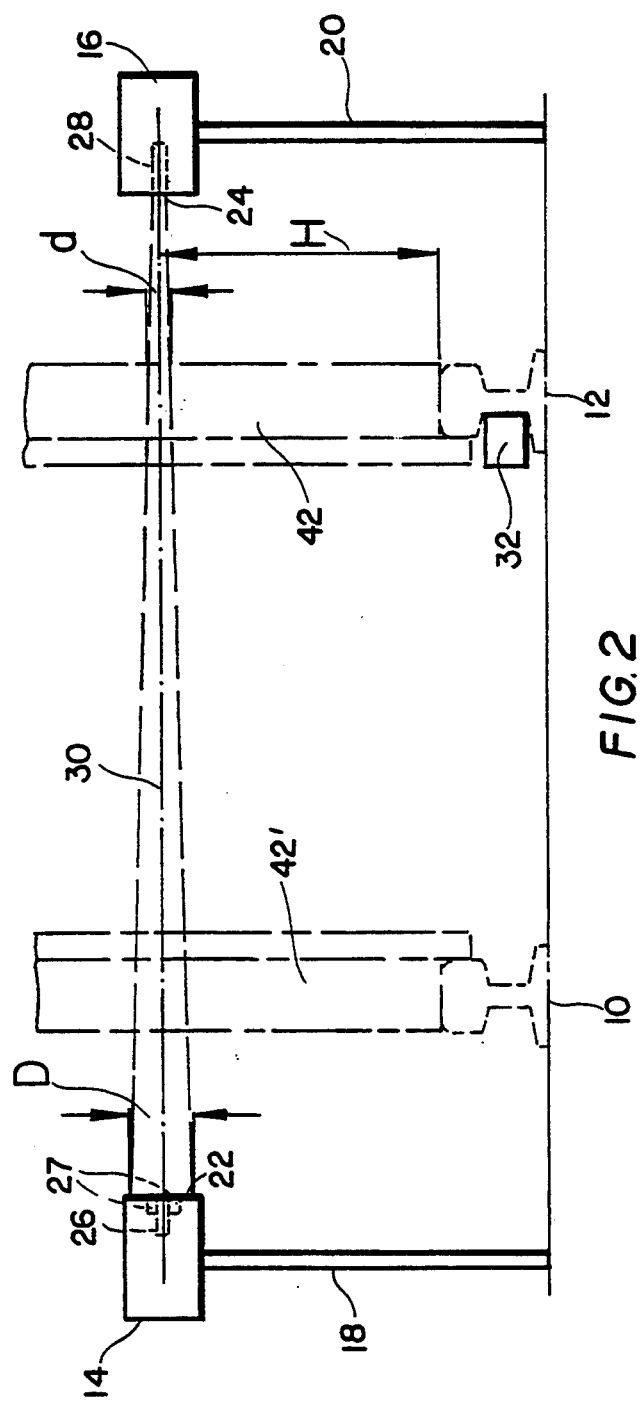
FIG. 2 shows a partial elevational view transversal to the tracks of the apparatus of FIG. 1.
Figure 3:
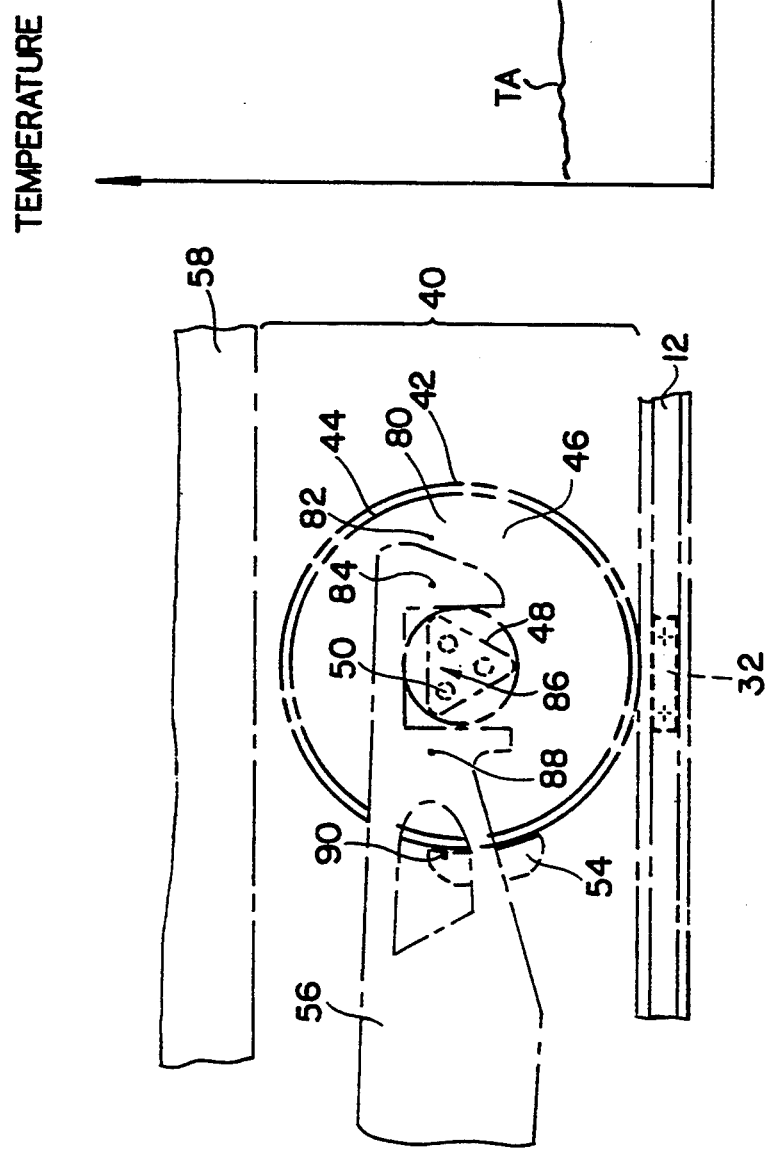
FIG. 3 shows a partial elevational view of a typical freight car truck with roller bearings.

Referring now to the drawings, the railroad track of FIGS. 1-3 includes two parallel rails 10, 12. Adjacent to the rails are two housings 14, 16 supported on respective uprights 18, 20.

Preferably uprights 18, 20 are hollow cylindrical mounting posts arranged and constructed to provide vertical air flow from the right of way to the housings 14, 16. These posts provide a chimney effect to compensate for the temperature gradient from below ground to above ground. In the summer, hot air from the top of the posts is vented out (through vent holes, not shown) allowing cool air to rise from the ground level. In the winter, warmer air from below ground rises through the post and warms the housings.

Each of the housings has front surfaces 22, 24. The housings are arranged so that the surfaces 22, 24 are facing each other across the tracks 10, 12, as shown. The housings 14, 16 contain infrared (IR) scanners 26, 28 of a conventional type for detecting temperature. The scanners are aligned along a common optical axis 30, so that, in the absence of an obstacle between the housings, each scanner monitors the front surface of the opposite housing. Axis 30 is disposed in a horizontal plane and is perpendicular to rails 10, 12. At least one of the rails, such as rail 12, is equipped with a wheel detector 32 for detecting the wheels of a train.

The truck for a typical freight car with roller bearings is shown in FIG. 3. It is estimated that about 95% of all freight cars presently in use in the United States are equipped with these kinds of roller bearings. The truck 40 includes a wheel 42 having a rim 44 and a web 46. The wheel 42 is supported on an axle (not shown) by roller bearings having an end cap 48. The end cap 48 is maintained in place by at least three bolts 50 which penetrate into the journal itself. A brake shoe 54 is mounted behind the wheel and is selectively applied against the rim 44. A typical truck may have two such wheels 42 on each side. A frame 56 is used to hold the wheels together. The body 58 of the car rides on top of the truck 40 on springs which have been omitted for the sake of clarity.

It has been found that since the bolts 50 penetrate into the journal, their temperature, and/or the temperature of the end cap 48 gives an accurate indication of the condition of the bearings. Therefore the scanners 26, 28 are positioned so that when wheels 42, 42' pass the scanners, the scanners read the temperature of the wheels along an imaginary horizontal zone traversing the end cap 48. Generally freight cars use wheels ranging from 28" to 38" in diameter. Scanners 26, 28 are positioned so that their optical axis 30 is disposed at a height H of 15¾" from the top of the rails 10,12. It was found that at this height the scanners can monitor the wheels having a diameter within the range mentioned defined above. The scanner includes optical means arranged to scan a spot d of about ⅜ in diameter on the bearings and wheels. When there is no train on the tracks, or when not viewing a truck, each scanner is arranged to monitor a spot D of about 6"in diameter on the front surfaces 22, 24.

If necessary, an electrically heated de-icing ring 27 may be disposed around the scanner 26 to remove ice that may accumulate thereon during the winter. A similar ring is provided for scanner 28 but has been omitted for the sake of clarity. Advantageously, the circle of area D viewed by scanner 28 has a much larger surface area than the surface area of ring 27 so that the ring 27 has no effect on the readings by scanner 28.

Figure 5:
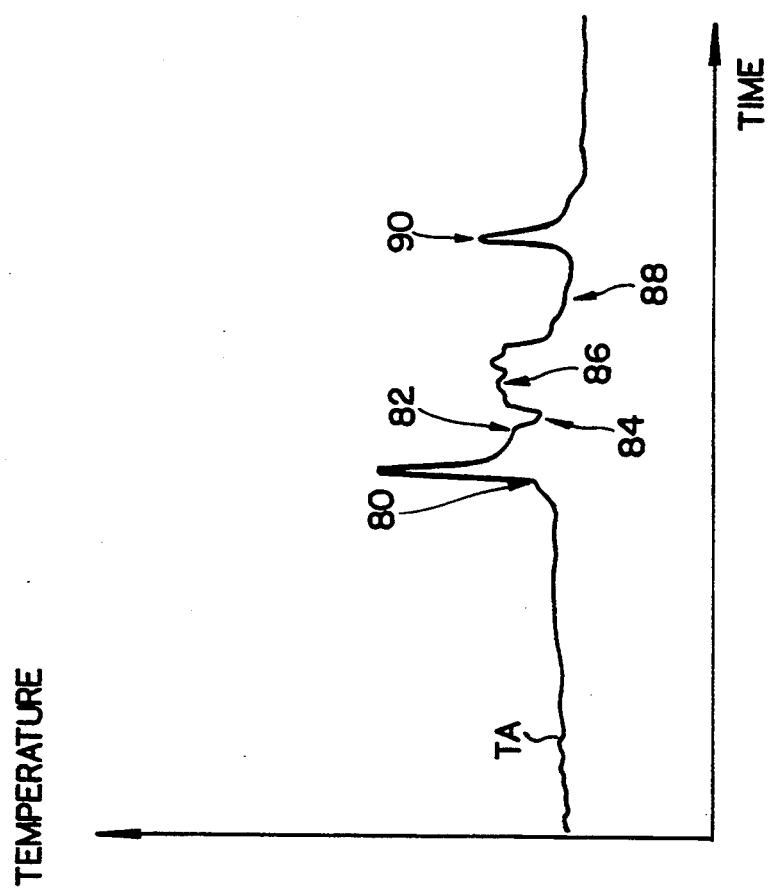
FIG. 5 shows a graph of a temperature profile obtained by the subject detector apparatus.

The operation of the detector apparatus shall now be described in conjunction with the FIGS. 4 and 5.

Figure 4:
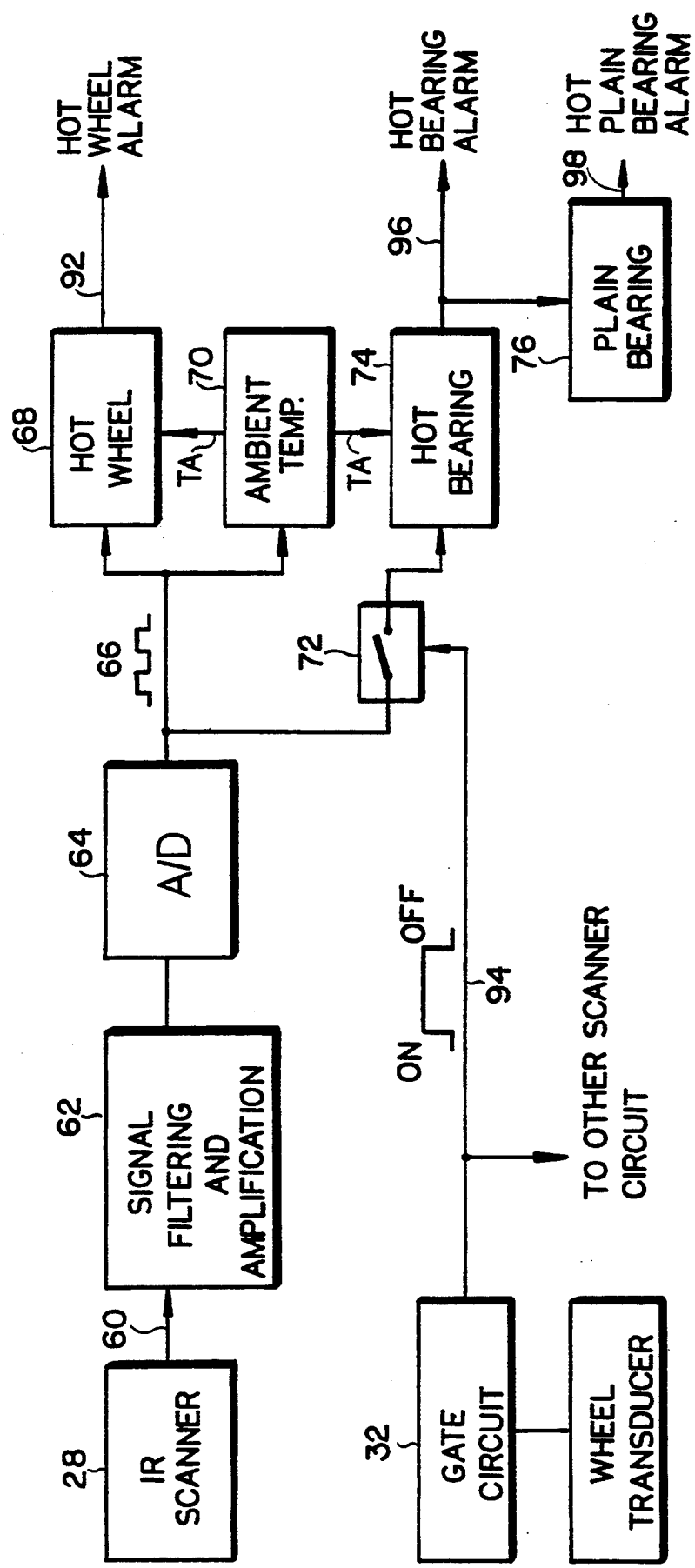
FIG. 4 shows a schematic block diagram for the detector apparatus.

FIG. 4 shows the detector circuitry for scanner 28. A similar circuitry is used for the scanner 26. IR scanner 28 monitors either a wheel 42 or the opposing face surface 22 and generates a continuous analog temperature signal 60. This signal is conditioned by filtering and amplifier stage 62. Preferably, stage 62 is A.C. coupled having a low-frequency response in the order of 0-0.06 Hz. The output of circuit 62 is converted into a digital form by A/D converter 64 to generate a binary data stream 66. This stream is fed to three circuits: a hot wheel determination circuit 68, a reference temperature circuit 70 and a switch 72.

FIG. 6 shows a typical temperature profile of a wheel 42 taken by sensor 28. More specifically, the profile of FIG. 6 shows the temperature of points 80, 82, 84, 86, 88 and 90 of FIG. 4. As shown in FIGS. 3 and 5, the temperature of wheel rim 80 and brake shoe 90 are relatively high. The temperature of web 46 and frame 56 (points 82, 84, 88) is somewhat lower and the temperature of end cap 48 (point 86) is higher then the temperature of the web. All these temperatures are evaluated with respect to an ambient temperature TA derived as described below.

As previously mentioned, in between wheels, or trains, scanner 28 monitors opposing front surface 22. The output of the scanner 28, after conditioning and A/D conversion, is fed to circuit 70 which uses this data to set the ambient temperature level TA. Importantly, since front surface 22 is vertical, it is relatively unaffected by weather conditions, such as rain, snow, or direct sun light and hence it is substantially at ambient temperature. Further, standard infrared techniques are used to minimize the emissivity of the scanner front surfaces via polishing and low emissivity coating of surfaces 22, 24. Moreover, even if the surface 22 has been heated by the sun, or cooled by snow or rain drops, as a train passes, winds produced by the train warm or cool the surface 22 to ambient temperature. During the winter the scanners 26, 28 may be heated electrically to eliminate any ice or snow deposited thereon. However, typically, these heaters are disabled while a train is passing to insure that the scanners take proper readings.

Hot wheel detector circuit 68 monitors data signals 66 continuously and after biasing them in accordance with the ambient temperature signal TA from circuit 70, it compares them to a preselected threshold level. If these data signals 66 exceed the threshold, a hot wheel alarm signal 92 is generated to indicate a hot wheel condition.

As the wheel 42 approaches and passes over wheel transducer 32, transducer 32 generates a substantially rectangular signal 94 coincident with the passing of end cap 48 past scanner 28. Signal 94 is used to close switch 72 thereby gating the data signals 66 to hot bearing circuit 74. The circuit 74 biases these signals to compensate for the ambient temperature TA and then compares them to a threshold level. If the threshold level is exceeded circuit 74 generates a hot bearing alarm signal 96 to indicate that a wheel with hot bearings has been detected. The data from switch 72 may also be fed to a plain bearing circuit 76 which analyzes this output to determine if the data signals 66 are characteristic of plain bearings, and whether the plain bearing is hot. Circuit 76 then generates a hot plain bearing signal 98.

In its most simplistic form, real time analog processing is possible with plain bearing recognition based on amplitude signal level and a different alarm criterion for each bearing type. Also, both roller bearing and plain bearing signals may be fed into a common absolute amplitude alarm circuit, thus maintaining independent operation for each side of the train.

Preferably since the two scanners 26, 28 are aligned transversely across the rail, a single wheel transducer 32 may be used for both scanner circuits. A gate width of 7" along the rail allows the gate to open and close while the scanner is still viewing the bearing—an ideal condition.

In the embodiment shown in FIG. 4, only the data signals corresponding to the temperature of the end cap 48 or plain bearing lid (point 86) are gated by switch 72 to circuit 74. However, the hot wheel circuit 68 receives the temperature signals indicating the temperature of both the wheel rim 44 and the end cap 48. Because normally the wheel rims run at much higher temperatures then the end caps, even when overheated, an end cap or a plain bearing housing lid will not register as a hot wheel. A typical overheated end cap may have a temperature of 200° F. while a typical overheated wheel rim may have a temperature of about 600° F.

The arrangement described above has numerous advantages over the prior art detectors having scanners disposed on the rail bed and oriented along the rails 10, 12. The arrangement permits a much shorter lens-to-bearing distance which is much more effective in poor weather, for example in swirling or accumulating snow. In fact it will take over 15" of snow or water to interfere directly with the scanner operation. The prior art scanners were incapacitated by water entrance due to poor drainage, or snow or ice deposited on the scanners by the action of snowplows.

Further snow and ice accumulating on the freight and passenger truck structures impedes the view of prior art scanners. No such impediment occurs with the right angle scanner.

The prior art scanners and junction boxes were difficult to remove from the road bed and hence they precluded tamping in the area of the detector. The present apparatus is clear of the tamping machine and only transducer removal is necessary to permit machine tamping. Failure to tamp in the detector area results in roadbed instability evidenced by rail pumping.

Unlike the prior art scanners, the present apparatus is not affected by changes in the rail size, rail cant and other rail variations therefore it can be easily standardized.

Unlike the prior art scanners, the present apparatus is out of the range of and not affected by dragging equipment The prior art scanners were reading either the leading or the lagging surfaces of the passing journal bearing boxes and had to have provisions for detecting the direction of train movement. The present apparatus scans transversely of the rails and is unaffected by train movement direction.

The present apparatus is removed from the rails and hence operates in a much cleaner environment. It is also immune from the large electromagnetic fields in electrified installations.

The positioning of the apparatus reduces the chance of it being damaged during a wheel off-the-rail condition. Damage will only occur when the off-rail wheel causes train derailment.

Obviously numerous other modifications may be made to this invention without departing from its scope as defined in the appended claims.

I claim:

1. A detector apparatus for monitoring the wheels of a railroad car running on tracks, said wheels having rims, bearing end caps or housings covering the wheel bearings, said detector apparatus comprising:
    scanning means disposed adjacent to said tracks and arranged and constructed to scan said wheels a direction normal to said tracks, said scanning means generating sequential data signals including rim temperature signals and end cap or housing lid temperature signals indicative of the temperature of said rims and said bearings respectively; and
    analyzing means for separating signals generated from scanning said rims and bearing structures and for analyzing said rim and bearing temperature signals, said analyzing means generating a hot wheel alarm signal when said rim temperature signals exceed a first threshold, and a hot bearing alarm signal when said bearing temperature signals exceed a second threshold.

2. The apparatus of claim 1 further comprising a stationary surface disposed adjacent to said tracks and arranged to be viewed by said scanning means to establish an ambient temperature, said analyzing means biasing said rim and cap temperature signals in accordance with said ambient temperature.

3. The apparatus of claim 2 wherein said scanning means is arranged and constructed to view a spot on said wheels having a first diameter and another spot on said surface having a second diameter larger than said first diameter.

4. The apparatus of claim 1 wherein said scanning means scans said wheels along a substantially horizontal axis.

5. The apparatus of claim 1 wherein said scanning means includes a first scanner disposed on one side of said tracks and a second scanner disposed on the other side of said tracks, said first and second scanners scanning said wheels along a common optical axis.

6. The apparatus of claim 5 wherein said common optical axis is substantially horizontal.

7. The apparatus of claim 5 further comprising a first and second housing for holding said first and second scanner respectively, said second housing having a side surface and said first scanner being arranged to scan said side surface for determining an ambient temperature.

8. The apparatus of claim 7 wherein said housings are mounted on hollow support members arranged and constructed to provide heat exchange with ground.

9. A detector apparatus for detecting the temperature along an imaginary horizontal line along the wheels of a train moving on tracks, said wheels including rims and roller bearing end caps or plain bearing housing lids, said apparatus comprising;
    a first scanner disposed on one side of said tracks;
    a second scanner disposed on the other side of said tracks;
    said scanners being constructed and arranged to scan said wheels along a common substantially horizontal optical axis and generate respective sequential temperature signals including rim temperature signals and bearing temperature signals; and
    analyzing means for analyzing said temperature signals and for generating a hot wheel and a hot bearing signal indicative of a hot wheel and a hot bearing condition respectively.

10. The apparatus of claim 9 wherein said optical axis is disposed at a preselected distance above said tracks.

11. The apparatus of claim 9 further comprising a first housing for holding said first scanner and having a first housing surface, and a second housing for holding said second scanner and having a second housing surface, said first and second scanners being arranged to view said second housing surface and said first housing surface respectively to establish an ambient temperature.

12. The apparatus of claim 11 wherein said housing surfaces are coated to provide a low emissivity scanner front surface to closely simulate an ambient radiation level.

13. The apparatus of claim 9 further comprising wheel detecting means for detecting said wheels.

14. A detector apparatus for detecting the temperature of the wheel rims and wheel bearings on a moving train, said apparatus comprising:
   scanning means for scanning each wheel along a substantially horizontal scan axis for generating sequentially wheel rim temperature signals and wheel bearing temperature signals indicative of the temperature of said wheel rims and wheel bearings respectively;
   means for separating said wheel rim temperature signals from said wheel bearing temperature signals;
   first circuit means for analyzing said rim temperature signals to generate a hot wheel alarm signal;
   second circuit means for analyzing said wheel bearing signals to generate a hot bearing alarm signal; and
   gating means gating said wheel bearing temperature signals to said second circuit means.

15. The apparatus of claim 14 wherein said scanning means is stationary, said apparatus further comprising wheel detection means for detecting said wheels, said wheel detecting means activating said gating means.

16. The apparatus of claim 14 wherein said second circuit means includes plain bearing means for detecting plain bearings.

17. The apparatus of claim 14 wherein said scanning means includes ambient temperature means for establishing an ambient temperature.

18. The apparatus of claim 17 wherein said first and second circuit means bias said temperature signals in accordance with said ambient temperature.

19. The apparatus of claim 14 further comprising a.c. coupled amplifier means for amplifying said temperature signals.

20. The apparatus of claim 19 wherein said amplifying means is responsive to signals in the range below 0.10 Hz.

* * * * *